United States Patent
Long

(10) Patent No.: US 7,754,249 B2
(45) Date of Patent: Jul. 13, 2010

(54) HAIRCARE COMPOSITIONS AND METHODS

(75) Inventor: Stewart Paul Long, Oakham (GB)

(73) Assignee: The Boots Company PLC, Nottingham (GB)

(*) Notice: Subject to any disclaimer, the term of this patent is extended or adjusted under 35 U.S.C. 154(b) by 297 days.

(21) Appl. No.: 11/629,773

(22) PCT Filed: Jun. 14, 2005

(86) PCT No.: PCT/GB2005/002351

§ 371 (c)(1),
(2), (4) Date: Dec. 15, 2006

(87) PCT Pub. No.: WO2005/123032

PCT Pub. Date: Dec. 29, 2005

(65) Prior Publication Data

US 2007/0141019 A1    Jun. 21, 2007

(30) Foreign Application Priority Data

Jun. 15, 2004 (GB) ................... 0413259.3
Apr. 13, 2005 (GB) ................... 0507439.8

(51) Int. Cl.
A61K 36/00 (2006.01)
A61K 8/97 (2006.01)
A61K 36/28 (2006.01)
A61K 9/00 (2006.01)

(52) U.S. Cl. ............ 424/725; 424/74; 424/764; 424/400

(58) Field of Classification Search ............ None
See application file for complete search history.

(56) References Cited

U.S. PATENT DOCUMENTS

| | | | |
|---|---|---|---|
| 4,288,433 A | 9/1981 | Koulbanis et al. | |
| 5,215,759 A | 6/1993 | Mausner | |
| 5,523,090 A | 6/1996 | Znaiden et al. | |
| 5,827,853 A | 10/1998 | Blanck-Ferras et al. | |
| 2001/0016213 A1 | 8/2001 | Singh-Verma | |
| 2004/0171693 A1 | 9/2004 | Gan et al. | |

FOREIGN PATENT DOCUMENTS

| | | |
|---|---|---|
| DE | 4312109 A1 | 10/1994 |
| DE | 43 30 597 A1 | 3/1995 |
| EP | 0629397 A1 | 12/1994 |
| EP | 1260212 A1 | 11/2002 |
| FR | 2 606 634 A | 5/1988 |
| FR | 2 751 541 A | 1/1998 |
| JP | 7010722 A | 1/1995 |
| JP | 2003026560 A | 1/2003 |
| WO | WO 00/53176 A | 9/2000 |
| WO | WO 01/17498 A | 3/2001 |
| WO | WO 01/19158 A2 | 3/2001 |
| WO | 02080880 A2 | 10/2002 |
| WO | WO 2004/078117 A | 9/2004 |
| WO | 2005102373 A2 | 11/2005 |

OTHER PUBLICATIONS

DW-ACC 1996-070555, Dec. 1995, EP, Melin.*
DW ACC 1988-221339, Aug. 1988, EP, Nogues.*
DW ACC 2002-124286, Jan 2002, EP, Charriere et al.*
DW ACC 2001-392626, Feb. 2001, JP, Imamura.*
De Maria et al., Composition of green coffee fractions and their contribution to the volatile profile formed during roasting, Food Chemistry, 1994, 141-145, 50.
Guyot et al., Esterification of phenolic acids from green coffee with an immobilized lipase from *Candida antarctica* in solvent-free medium, Biotechnology Letters, 1997, 529-532, 19.
Srivastava et al., Chemistry and pharmacology of *Centella asiatica*: A review. Journal of Medicinal and Aromatic Plant Sciences, 1997, 1049-1056, 19.

* cited by examiner

*Primary Examiner*—Christopher R Tate
*Assistant Examiner*—Randall Winston
(74) *Attorney, Agent, or Firm*—Rothwell, Figg, Ernst & Manbeck, P.C.

(57) ABSTRACT

Compositions and methods are disclosed for use in the treatment or prevention of hair loss and/or the promotion of hair growth. The compositions comprise in combination *Centella asiatica* extract, or one or more active principles thereof, green coffee extract, or one or more active principles thereof, and one or more antioxidants, and a dermatologically acceptable carrier.

15 Claims, No Drawings

HAIRCARE COMPOSITIONS AND METHODS

CROSS REFERENCE TO RELATED APPLICATION

This application is a 35 USC §371 National Phase Entry Application from PCT/GB2005/002351, filed Jun. 14, 2005, and designating the United States.

The present invention relates to haircare compositions and methods, and in particular to compositions and methods that are of use in the treatment or prevention of hair loss and/or the promotion of hair growth.

Common baldness, or alopecia, is characterized as a patterned, progressive and, until recently, largely irreversible loss of an excessive amount of hair from the scalp. Significant alopecia occurs in 50% of men by the age of 50 and 50% of women by the age of 60 years. More limited hair loss affects all men and women from late teens onwards. The major prerequisites identified for common baldness are a genetic predisposition and the influence of androgens. The pattern of hair loss experienced by men and women tends to follow different patterns. Hamilton described the distinctive pattern of progression of hair loss in men and graded the severity on a scale of I to VIII. Alteration of the frontal hair line with bitemporal recession usually occurs first, leading to balding of the vertex. In women, Hamilton-type balding also occurs, with up to 79% progressing to grade II on the scale after puberty and 25% developing grade V by age 50 years. However, more commonly, female hair loss results in diffuse loss across the crown with preservation of the frontal hair line. This pattern of hair loss is graded using the scale devised by Ludwig.

The term "hair loss" is used herein to encompass all forms of hair thinning and shedding.

Treatment of alopecia ranges from camouflage measures, such as hairpieces and wigs, colouring the scalp to disguise thinning, and cosmetic thickening products to give the illusion of greater hair volumes, through to medical intervention, such as hair transplants and treatment with drugs such as finasteride and minoxidil. The latter treatments with anti-androgenic drugs such as minoxidil and finasteride are variably successful in slowing or reversing hair loss, but can have side effects that are undesirable. Side effects with minoxidil include pruritus and contact allergic dermatitis. Side effects of finasteride include lowered male libido and erectile dysfunction. Trials in women show only limited success of finasteride in slowing hair loss, and it is a teratogen, posing a risk to the unborn child.

Numerous treatments for hair loss are thus currently available, but many consumers would prefer alternative, safer products that are easy and pleasant to use, and are aesthetically pleasing once applied. Consumers may also prefer products in which natural ingredients are used.

Natural extracts of green coffee and *Centella asiatica*, also known as Indian Pennywort or Gotu Kola, have been known for some time to be of potential utility in the treatment of hair loss.

FR-2721506, DE-4330597 and DE 4312109 all disclose compositions containing coffee extract, and that those compositions may have an effect on hair loss.

Compositions to prevent hair loss and promote re-growth, and which contain extract from Centella asiatica, are described in EP-0277455 and FR-2606634. JP-7010722 also discloses a hair tonic containing *Centella asiatica* extract.

US 2004/0171693 relates to methods for stimulating hair follicle growth, comprising the application of a composition containing a follicle-stimulating effective amount of creatine or a creatine derivative.

Compositions containing caffeine and *Centella asiatica* are also disclosed in U.S. Pat. Nos. 5,827,853 and 4,288,433 in relation to anti-cellulite and/or slimming compositions.

None of these hair loss compositions have been found to be entirely satisfactory. Given the high prevalence of premature hair loss and the psychological impact it has on sufferers, there exists a need for a more effective hair loss treatment that contains natural or naturally-derived compounds which may provide a safer alternative to the treatments currently available, and which retain usability and suitable aesthetic properties. Surprisingly, it has been found that by combining *Centella asiatica* extract, green coffee extract and an antioxidant, or at least two of these components, superior compositions can be produced.

According to the invention there is provided a composition for the treatment or prevention of hair loss and/or the promotion of hair regrowth, which composition comprises in combination *Centella asiatica* extract, or one or more active principles thereof, green coffee extract, or one or more active principles thereof, and one or more antioxidants, and a dermatologically acceptable carrier.

The compositions according to the invention are advantageous because the combinations of active ingredients are naturally-derived and may be more efficacious than the prior art. The actives may be safer than currently available treatments. In addition or alternatively, the compositions may be easy to use and may have pleasing sensory and/or aesthetic properties.

In particularly preferred embodiments, the compositions may exhibit synergistic properties, the effect of the combined active ingredients being greater than would be expected on the basis of the effects of those ingredients individually.

Compositions of the invention are preferably substantially free of caffeine.

A further group of preferred compositions are substantially free of a creatine compound.

The term "creatine compound" refers to both creatine and creatine derivatives or analogues that may exhibit similar activity, eg creatine phosphate or cyclocreatine.

By "substantially free" is meant in the context of the present invention that the composition does not comprise an effective amount of the ingredient that would be recognized as having a significant effect in the treatment or prevention of hair loss and/or promotion of hair growth. In general, this means that the composition will contain less than 0.2% by weight of the ingredient, preferably less than 0.1% by weight, and most preferably less than 0.001% by weight.

The concentration of *Centella asiatica* extract in the composition according to the invention is preferably at least 0.05% by weight, more preferably at least 0.1%. The concentration of *Centella asiatica* extract is preferably less than 5% by weight, more preferably less than 3%, and most preferably less than 1%. The concentration of *Centella asiatica* extract may therefore fall in the range 0.05% to 5% by weight, more preferably 0.1% to 3%, and most preferably 0.1% to 2%. Particularly preferred concentrations of *Centella asiatica* extract are 0.25%, 0.5%, 0.75% and 1% by weight.

*Centella asiatica* may be incorporated in the composition according to the invention as an entire extract, ie a natural extract containing the active principles in combination with numerous other molecules. Alternatively, one or more specific active ingredients found in such an extract may be utilised. Such active ingredients may be isolated from the natural extract, or may be synthetic in origin, ie the active ingredients may be synthetic materials identical in structure, or substantially so, to material of natural origin.

Examples of active principles that may be isolated from *Centella asiatica* extract, or which may be used in synthetic form, are triterpenic acids, eg asiatic acid and madecassic acid, or derivatives, particularly esters, thereof, notably carbohydrate esters such as the asiatic acid derivative known as asiaticoside. The extract may be water or oil soluble. A typical water soluble extract is composed of 94% *Centella asiatica* extract, mainly in the form of asiaticoside or madecassoside and is available commercially from Roche Serdex.

The concentration of green coffee extract in the composition according to the invention is preferably at least 0.02% by weight on a dry weight basis (dwt), more preferably at least 0.04% by weight (dwt). The concentration of green coffee extract is preferably less than 0.6% by weight (dwt), more preferably less than 0.4% by weight (dwt) and most preferably less than 0.3% by weight (dwt). The concentration of green coffee extract may therefore fall in the range 0.02 to 0.6% by weight (dwt), more preferably 0.04 to 0.4% by weight (dwt), and most preferably 0.04 to 0.3% by weight (dwt). Particularly preferred concentrations of green coffee are 0.12, 0.16, 0.2 and 0.3% by weight (dwt).

Examples of active principles that may be isolated from green coffee extract, or which may be used in synthetic form, are non-volatile acids, eg chlorogenic acid, caffeine, trigonelline or carbohydrates such as cellulose derivatives, sugars and starches. Cellulose derivatives may be hemi-celluloses and holocellulose. The extract may be a liquid extract or freeze/spray dried. A typical liquid extract may have approximately 4% actives on a dry matter basis. Suitable extracts are available commercially.

The combined concentration of one or more antioxidants in the composition preferably ranges from 0.005% to 10% by weight, more preferably 0.05% to 5%, most preferably 0.1% to 2% by weight of the composition.

By "antioxidant" is generally meant in the context of the present invention a compound that will terminate free-radical induced reactions, thus reducing or preventing oxidative damage.

A wide range of antioxidants may be suitable for inclusion in the composition according to the invention. These include:
a) Vitamin C (ascorbic acid) its salts, esters, glucosides and glucosamines, particularly sodium ascorbyl phosphate, magnesium ascorbyl phosphate and ascorbyl palmitate, and other sources eg Acerola cherry powder.
b) Vitamin E (tocopherol) and its esters, particularly tocopheryl acetate.
c) Other vitamins and minerals eg CoQ10, selenium, magnesium, copper and zinc.
d) Carotenoids eg beta-carotene, lutein and lycopene.
e) Polyphenolics eg from *Camellia sinensis* (Green Tea), *Pyrus malus* (apple), rosamarinic acid and pycnogenol.
f) Herbal extracts eg *Gingko biloba, Morus alba* (mulberry), *Origanum vulgare* (oregano), *Panax ginseng* (ginseng), *Rosmarinus officinalis, Salvia officinalis* (sage) extract, *Ziziphus spina-christi* and *Vitis vinifera* (grape seed).
g) Synthetic antioxidants such as butylated hydroxytoluene (BHT) and butylated hydroxyanesole (BHA).

Preferred antioxidants include sodium and magnesium ascorbyl phosphate, *Panax ginseng, Morus alba, Origanum vulgare* and *Rosmarinus officinalis* extracts.

The composition according to the invention may include one antioxidant, or a combination of two or more antioxidants.

Particularly preferred antioxidant agents are sodium ascorbyl phosphate, and *Rosmarinus officinalis* extract or a combination thereof.

The composition according to the invention may additionally comprise other ingredients which will be well known to those skilled in the art. These include, for example:
a) Surfactants—emulsifiers, solubilisers, wetting and cleaning agents, foam producers and conditioning agents. Examples of surfactants include sodium laureth sulphate, cocamidopropyl betaine, and sodium cocoamphoacetate.
b) Excipients to enhance texture and skin-feel, such as xanthan gum, carbomer, and silicones.
c) Vitamins or additional natural extracts, for example the provitamin, D-panthenol, is often beneficial in haircare compositions.
d) Preservatives—ingredients which prevent or retard microbial growth and thus protect the composition from spoilage. Examples of preservatives include such as propylparaben, methylparaben, phenoxyethanol, sodium benzoate, bronopol, sodium dehydroacetate, polyhexamethylenebiguanide hydrochloride, isothiazolinones and diazolidinylurea.
e) Chelating agents or sequestering agents (sequestrants)—ingredients that have the ability to complex with and inactivate metallic ions in order to prevent their adverse effects on the stability or appearance of the composition. Examples of chelating agents are ethylenediamine tetraacetic acid and its salts, notably the dipotassium and especially the disodium or tetrasodium salt.
f) Perfumes and colourings.

The composition according to the invention may have any one of a wide variety of forms, which will be determined by the nature of the dermatologically acceptable carrier. Suitable forms that the composition may take include a gel, lotion, spray, shampoo or conditioner.

The determatologically acceptable carrier according to the invention may be aqueous, or lipid-based, or may comprise both an aqueous phase and an oil phase. Aqueous compositions may, for example, have the form of a solution or dispersion in water, or in a mixed solvent comprising water and a cosolvent, eg a lower alcohol. Such a composition may be applied as a spray. The composition may also take the form of a gel. Other compositions according to the invention may be formulated as emulsions, eg shampoo and conditioner formulations.

In another aspect of the invention, there is provided a method for the treatment or prevention of hair loss and/or the promotion of hair regrowth, which method comprises the application to the skin of a composition as described above.

Most commonly, the area of the skin to which the composition is applied will be the scalp, ie the composition will be used to combat hair loss on the user's head.

In addition to treating or preventing hair loss and/or promoting the growth of the hair, the method of the invention may also improve the appearance of hairs to which the composition is applied, eg by thickening the hair and improving the lustre, condition and manageability of the hair.

The composition may be applied to skin and hair using any suitable treatment regime.

Compositions according to the invention are preferably applied at least once a week, more preferably at least every two days, and most preferably at least once each day. Application twice per day is particularly preferred.

In general, treatment using the composition according to the invention may be continued indefinitely. Alternatively, the treatment may be repeated only for a limited period, eg several weeks or months. Treatment may then be repeated for a similar period at a later date.

After application to the skin, the composition may be rinsed off, or may be left on the skin (and hair). If the composition is to be rinsed off after application, it is preferred that the composition is left on for a minimum period of time before rinsing. This preferred period of time is more than 30 seconds, more preferably more than 1 minute, and most preferably more than 3 minutes.

It is also preferred that the product is massaged into the skin, most commonly into the scalp, during application, preferably for at least 5 seconds, more preferably for at least 20 seconds.

Particularly beneficial results may be obtained by the use of two or more different forms of composition concurrently. For example, for the treatment or prevention of hair loss and/or the promotion of hair regrowth on the head, a user may wash their hair with a shampoo and then use a conditioner, both the shampoo and the conditioner constituting compositions according to the invention, the user massaging each product into their scalp before rinsing. The user may subsequently apply another form of composition according to the invention, eg a gel or lotion, directly to the scalp with gentle massage, that composition being left on the head until the user next washes their hair.

It has also been found that certain compositions are effective, which contain only two out of the three active ingredients mentioned above. Thus, according to a further aspect of the invention there is provided a composition for the treatment or prevention of hair loss and/or the promotion of hair regrowth, which composition comprises in combination *Centella asiatica* extract, or one or more active principles thereof, green coffee extract, or one or more active principles thereof, and a dermatologically acceptable carrier, provided that if the composition contains 0.1% or 0.2% caffeine, then the composition is substantially free of a creatine compound.

In another aspect of the invention, there is provided a method for the treatment or prevention of hair loss and/or the promotion of hair regrowth, which method comprises the application to the skin of a composition comprising two or more active ingredients selected from the group consisting of *Centella asiatica* extract, or an active principle thereof, green coffee extract, or an active principle thereof, and one or more antioxidants, and a dermatologically acceptable carrier, provided that if the composition contains 0.1% or 0.2% caffeine, then the composition is substantially free of a creatine compound.

One preferred embodiment of the invention is a method for the treatment or prevention of hair loss and/or the promotion of hair regrowth, which method comprises the application to the skin of a composition comprising *Centella asiatica* extract, or one or more active principles thereof, and green coffee extract, or one or more active principles thereof, provided that if the composition contains 0.1% or 0.2% caffeine, then the composition is substantially free of a creatine compound.

A further preferred embodiment of the invention is a method for the treatment or prevention of hair loss and/or the promotion of hair regrowth, which method comprises the application to the skin of a composition, wherein the composition comprises *Centella asiatica* extract, and green coffee extract.

Another preferred embodiment of the invention for the treatment or prevention of hair loss and/or the promotion of hair regrowth, which method comprises the application to the skin of a composition, wherein the composition comprises *Centella asiatica* extract, and one or more antioxidants.

Another preferred embodiment of the invention for the treatment or prevention of hair loss and/or the promotion of hair regrowth, which method comprises the application to the skin of a composition, wherein the composition comprises green coffee extract, and one or more antioxidants.

The invention will now be described in greater detail, by way of illustration only, with reference to the following Examples.

Example 1

Scalp Spray Formulation

| Ingredient | % w/w |
|---|---|
| D-panthenol | 1.00 |
| Benzophenone-4 | 0.10 |
| Butylene glycol | 5.00 |
| Phenoxyethanol | 0.40 |
| Methyl parabens (sodium salt) | 0.20 |
| Sodium benzoate | 0.20 |
| Green coffee extract (4% dry weight aq extract) | 5.00 |
| *Centella asiatica* (water soluble extract) | 0.50 |
| Denatured ethanol | 10.00 |
| Water | qs |

Method of Manufacture

Mix together water, benzophenone-4, phenoxyethanol, methyl parabens (sodium salt) and butylene glycol. Add d-panthenol, green coffee extract (4% dry weight aq extract) and *Centella asiatica* (water soluble extract). Add denatured ethanol.

Example 2

Scalp Spray Formulation

| Ingredient | % w/w |
|---|---|
| D-panthenol | 1.00 |
| Benzophenone-4 | 0.10 |
| Butylene glycol | 5.00 |
| Phenoxyethanol | 0.40 |
| Methyl parabens (sodium salt) | 0.20 |
| Sodium benzoate | 0.20 |
| Green coffee extract (4% dry weight aq extract) | 5.00 |
| *Rosmarinus officinalis* extract | 0.30 |
| Denatured ethanol | 10.00 |
| Water | qs |

Method of Manufacture

Mix together water, benzophenone-4, phenoxyethanol, methyl parabens (sodium salt) and butylene glycol. Add d-panthenol, green coffee extract (4% dry weight aq extract) and *Rosmarinus officinalis* extract. Add denatured ethanol.

Example 3

Scalp Spray Formulation

| Ingredient | % w/w |
| --- | --- |
| D-panthenol | 1.00 |
| Benzophenone-4 | 0.10 |
| Butylene glycol | 5.00 |
| Phenoxyethanol | 0.40 |
| Methyl parabens (sodium salt) | 0.20 |
| Sodium benzoate | 0.20 |
| Sodium ascorbyl phosphate | 0.30 |
| *Centella asiatica* (water soluble extract) | 0.50 |
| Denatured ethanol | 10.00 |
| Water | qs |

Method of Manufacture

Mix together water, benzophenone-4, phenoxyethanol, methyl parabens (sodium salt) and butylene glycol. Add d-panthenol, sodium ascorbyl phosphate and *Centella asiatica* (water soluble extract). Add denatured ethanol.

Example 4

Scalp Spray Formulation

| Ingredient | % w/w |
| --- | --- |
| D-panthenol | 1.00 |
| Benzophenone-4 | 0.10 |
| Butylene glycol | 5.00 |
| Phenoxyethanol | 0.40 |
| Methyl parabens (sodium salt) | 0.20 |
| Sodium benzoate | 0.20 |
| Green coffee extract (4% dry weight aq extract) | 5.00 |
| *Centella asiatica* (water soluble extract) | 0.50 |
| *Rosmarinus officinalis* extract | 0.30 |
| Sodium ascorbyl phosphate | 0.30 |
| Denatured Ethanol | 10.00 |
| Water | qs |

Method of Manufacture

Mix together water, benzophenone-4, phenoxyethanol, methyl parabens (sodium salt) and butylene glycol. Add d-panthenol, green coffee extract (4% dry weight aq extract), *Centella asiatica* (water soluble extract), *Rosmarinus officinalis* extract and sodium ascorbyl phosphate. Add denatured ethanol.

Example 5

Hair Gel Formulation

| Ingredient | % w/w |
| --- | --- |
| Carbomer | 0.80 |
| Benzophenone-4 | 0.02 |
| Glycerin | 1.00 |
| Butylene glycol | 4.00 |
| Phenoxyethanol | 0.40 |
| Methyl parabens (sodium salt) | 0.20 |
| Sodium benzoate | 0.20 |
| Green coffee extract (4% dry weight aq extract) | 5.00 |
| *Centella asiatica* (water soluble extract) | 0.50 |
| Sodium hydroxide | 0.09 |
| Water | qs |

Method of Manufacture

Mix together water, benzophenone-4, phenoxyethanol, methyl parabens (sodium salt), glycerin and butylene glycol. Add carbomer with stirring. When carbomer is fully hydrated add sodium hydroxide, green coffee extract (4% dry weight aq extract) and *Centella asiatica* (water soluble extract).

Example 6

Hair Gel Formulation

| Ingredient | % w/w |
| --- | --- |
| Carbomer | 0.80 |
| Benzophenone-4 | 0.02 |
| Glycerin | 1.00 |
| Butylene Glycol | 4.00 |
| Phenoxyethanol | 0.40 |
| Methyl parabens (sodium salt) | 0.20 |
| Sodium benzoate | 0.20 |
| Green coffee extract (4% dry weight aq extract) | 5.00 |
| *Rosmarinus officinalis* extract | 0.30 |
| Sodium hydroxide | 0.09 |
| Water | qs |

Method of Manufacture

Mix together water, benzophenone-4, phenoxyethanol, methyl parabens (sodium salt), glycerin and butylene glycol. Add carbomer with stirring. When carbomer is fully hydrated add sodium hydroxide, green coffee extract (4% dry weight aq extract) and *Rosmarinus officinalis* extract.

Example 7

Hair Gel Formulation

| Ingredient | % w/w |
| --- | --- |
| Carbomer | 0.80 |
| Benzophenone-4 | 0.02 |
| Glycerin | 1.00 |
| Butylene glycol | 4.00 |
| Phenoxyethanol | 0.40 |
| Methyl parabens (sodium salt) | 0.20 |
| Sodium benzoate | 0.20 |
| Sodium ascorbyl phosphate | 0.30 |
| *Centella asiatica* (water soluble extract) | 0.50 |
| Sodium hydroxide | 0.09 |
| Water | qs |

Method of Manufacture

Mix together water, benzophenone-4, phenoxyethanol, methyl parabens (sodium salt), glycerin and butylene glycol. Add carbomer with stirring. When carbomer is fully hydrated add sodium hydroxide, sodium ascorbyl phosphate and *Centella asiatica* (water soluble extract).

Example 8

Hair Gel Formulation

| Ingredient | % w/w |
|---|---|
| Carbomer | 0.80 |
| Benzophenone-4 | 0.02 |
| Glycerin | 1.00 |
| Butylene glycol | 4.00 |
| Phenoxyethanol | 0.40 |
| Methyl parabens (sodium salt) | 0.20 |
| Sodium benzoate | 0.20 |
| Green coffee extract (4% dry weight aq extract) | 5.00 |
| *Centella asiatica* (water soluble extract) | 0.50 |
| *Rosmarinus officinalis* extract | 0.30 |
| Sodium ascorbyl phosphate | 0.30 |
| Sodium hydroxide | 0.09 |
| Water | qs |

Method of Manufacture

Mix together water, benzophenone-4, phenoxyethanol, methyl parabens (sodium salt), glycerin and butylene glycol. Add carbomer with stirring. When carbomer is fully hydrated add sodium hydroxide, green coffee extract (4% dry weight aq extract), *Centella asiatica* (water soluble extract), *Rosmarinus officinalis* extract and sodium ascorbyl phosphate.

Example 9

Scalp Lotion Formulation

| Ingredient | % w/w |
|---|---|
| Xanthan Gum | 0.12 |
| Carbomer | 0.055 |
| EDTA tetra sodium salt | 0.02 |
| Methyl parabens | 0.20 |
| Glycerin | 3.00 |
| Silicone fluid | 2.50 |
| Glyceryl stearate | 1.27 |
| PEG-100 stearate | 1.23 |
| Cetyl alcohol | 1.00 |
| White soft paraffin | 1.00 |
| Liquid paraffin | 4.00 |
| Caprylic/Capric triglyceride | 3.00 |
| Propyl parabens | 0.10 |
| Phenoxyethanol | 0.60 |
| Green coffee extract (4% dry weight aq extract) | 5.00 |
| *Centella asiatica* (oil soluble extract) | 0.50 |
| Potassium hydroxide | 0.006 |
| Water | qs |

Method of Manufacture

Mix together xanthan gum and glycerin. To approximately 40% of the water add carbomer and stir to hydrate. With stirring add the premixed xanthan gum and glycerin. Add all other ingredients apart from green coffee extract (4% dry weight aq extract), *Centella asiatica* (water soluble extract) and potassium hydroxide. Heat to 70-75° C. to melt waxes. Homogenise for 5 minutes to emulsify. Add potassium hydroxide and homogenise for 1 minute. Add the balance of water slowly and continue stirring and cool to below 40° C. Add green coffee extract (4% dry weight aq extract) and *Centella asiatica* (water soluble extract).

Example 10

Scalp Lotion Formulation

| Ingredient | % w/w |
|---|---|
| Xanthan gum | 0.12 |
| Carbomer | 0.055 |
| EDTA tetra sodium salt | 0.02 |
| Methyl parabens | 0.20 |
| Glycerin | 3.00 |
| Silicone fluid | 2.50 |
| Glyceryl stearate | 1.27 |
| PEG-100 stearate | 1.23 |
| Cetyl alcohol | 1.00 |
| White soft paraffin | 1.00 |
| Liquid paraffin | 4.00 |
| Caprylic/Capric triglyceride | 3.00 |
| Propyl parabens | 0.10 |
| Phenoxyethanol | 0.60 |
| Green coffee extract (4% dry weight aq extract) | 5.00 |
| *Rosmarinus officinalis* extract | 0.30 |
| Potassium hydroxide | 0.006 |
| Water | qs |

Method of Manufacture

Mix together xanthan gum and glycerin. To approximately 40% of the water add carbomer and stir to hydrate. With stirring add the premixed xanthan gum and glycerin. Add all other ingredients apart from green coffee extract (4% dry weight aq extract), rosemary extract and potassium hydroxide. Heat to 70-75° C. to melt waxes. Homogenise for 5 minutes to emulsify. Add potassium hydroxide and homogenise for 1 minute. Add the balance of water slowly and continue stirring and cool to below 40° C. Add green coffee extract (4% dry weight aq extract) and *Rosmarinus officinalis* extract.

Example 11

Scalp Lotion Formulation

| Ingredient | % w/w |
|---|---|
| Xanthan gum | 0.12 |
| Carbomer | 0.055 |
| EDTA tetra sodium salt | 0.02 |
| Methyl parabens | 0.20 |
| Glycerin | 3.00 |
| Silicone fluid | 2.50 |
| Glyceryl stearate | 1.27 |
| PEG-100 stearate | 1.23 |
| Cetyl alcohol | 1.00 |
| White soft paraffin | 1.00 |
| Liquid paraffin | 4.00 |
| Caprylic/Capric triglyceride | 3.00 |

-continued

| Ingredient | % w/w |
| --- | --- |
| Propyl parabens | 0.10 |
| Phenoxyethanol | 0.60 |
| Sodium ascorbyl phosphate | 0.30 |
| *Centella asiatica* (oil soluble extract) | 0.50 |
| Potassium hydroxide | 0.006 |
| Water | qs |

Method of Manufacture

Mix together xanthan gum and glycerin. To approximately 40% of the water add carbomer and stir to hydrate. With stirring add the premixed xanthan gum and glycerin. Add all other ingredients apart from sodium ascorbyl phosphate, *Centella asiatica* (water soluble extract) and potassium hydroxide. Heat to 70-75° C. to melt waxes. Homogenise for 5 minutes to emulsify. Add potassium hydroxide and homogenise for 1 minute. Add the balance of water slowly and continue stirring and cool to below 40° C. Add sodium ascorbyl phosphate and *Centella asiatica* (water soluble extract).

Example 12

Scalp Lotion Formulation

| Ingredient | % w/w |
| --- | --- |
| Xanthan gum | 0.12 |
| Carbomer | 0.055 |
| EDTA tetra sodium salt | 0.02 |
| Methyl parabens | 0.20 |
| Glycerin | 3.00 |
| Silicone fluid | 2.50 |
| Glyceryl stearate | 1.27 |
| PEG-100 stearate | 1.23 |
| Cetyl alcohol | 1.00 |
| White soft paraffin | 1.00 |
| Liquid paraffin | 4.00 |
| Caprylic/Capric triglyceride | 3.00 |
| Propyl parabens | 0.10 |
| Phenoxyethanol | 0.60 |
| Green coffee extract (4% dry weight aq extract) | 5.00 |
| *Centella asiatica* (oil soluble extract) | 0.50 |
| *Rosmarinus officinalis* extract | 0.30 |
| Sodium ascorbyl phosphate | 0.30 |
| Potassium hydroxide | 0.006 |
| Water | qs |

Method of Manufacture

Mix together xanthan gum and glycerin. To approximately 40% of the water add carbomer and stir to hydrate. With stirring add the premixed xanthan gum and glycerin. Add all other ingredients apart from green coffee extract (4% dry weight aq extract), *Centella asiatica* (water soluble extract), rosemary extract and sodium ascorbyl phosphate and potassium hydroxide. Heat to 70 -75° C. to melt waxes. Homogenise for 5 minutes to emulsify. Add potassium hydroxide and homogenise for 1 minute. Add the balance of water slowly and continue stirring and cool to below 40° C. Add green coffee extract (4% dry weight aq extract), *Centella asiatica* (water soluble extract), *Rosmarinus officinalis* extract and sodium ascorbyl phosphate.

Example 13

Shampoo Formulation

| Ingredient | % w/w |
| --- | --- |
| Sodium laureth sulphate | 4.00 |
| Cocamidopropyl betaine | 1.20 |
| Sodium cocoamphoacetate | 2.40 |
| Citric acid | 0.15 |
| EDTA tetra sodium salt | 0.02 |
| Polyquaternium-10 | 0.30 |
| Propyl parabens | 0.10 |
| Methyl parabens | 0.20 |
| Phenoxyethanol | 0.85 |
| Quaternium 80 | 0.40 |
| Amodimethicone | 2.00 |
| Green coffee extract (4% dry weight aq extract) | 5.00 |
| *Centella asiatica* (water soluble extract) | 0.50 |
| D-panthenol | 1.00 |
| Acrylates/Palmeth-25 acrylate copolymer | 3.00 |
| Sodium hydroxide | 0.015 |
| Water | qs |

Method of Manufacture

To water add polyquaternium-10, EDTA tetra sodium salt, citric acid and quaternium 80. Add sodium laureth sulphate and cocamidopropyl betaine. Mix together phenoxyethanol, methyl parabens and propyl parabens and heat to 50° C. until dissolved. Add to main bulk. Add d-panthenol, amodimthicone and extracts. Add acrylates/palmeth-25 acrylate copolymer (pre dispersed in a little water) and cocoamphoacetate. Add sodium hydroxide.

Example 14

| Ingredient | % w/w |
| --- | --- |
| Sodium laureth sulphate | 4.00 |
| Cocamidopropyl betaine | 1.20 |
| Sodium cocoamphoacetate | 2.40 |
| Citric acid | 0.15 |
| EDTA tetra sodium salt | 0.02 |
| Polyquaternium-10 | 0.30 |
| Propyl parabens | 0.10 |
| Methyl parabens | 0.20 |
| Phenoxyethanol | 0.85 |
| Quaternium 80 | 0.40 |
| Amodimethicone | 2.00 |
| Green coffee extract (4% dry weight aq extract) | 5.00 |
| *Rosmarinus officinalis* extract | 0.30 |
| D-panthenol | 1.00 |
| Acrylates/Palmeth-25 acrylate copolymer | 3.00 |
| Sodium hydroxide | 0.015 |
| Water | qs |

Shampoo Formulation

Method of Manufacture

To water add polyquaternium-10, EDTA tetra sodium salt, citric acid and quaternium 80. Add sodium laureth sulphate and cocamidopropyl betaine. Mix together phenoxyethanol, methyl parabens and propyl parabens and heat to 50° C. until dissolved. Add to main bulk. Add d-panthenol, amodimthicone and extracts. Add acrylates/palmeth-25 acrylate copolymer (pre dispersed in a little water) and cocoamphoacetate. Add sodium hydroxide.

Example 15

Shampoo Formulation

| Ingredient | % w/w |
| --- | --- |
| Sodium laureth sulphate | 4.00 |
| Cocamidopropyl betaine | 1.20 |
| Sodium cocoamphoacetate | 2.40 |
| Citric acid | 0.15 |
| EDTA tetra sodium salt | 0.02 |
| Polyquaternium-10 | 0.30 |
| Propyl parabens | 0.10 |
| Methyl parabens | 0.20 |
| Phenoxyethanol | 0.85 |
| Quaternium 80 | 0.40 |
| Amodimethicone | 2.00 |
| Sodium ascorbyl phosphate | 0.30 |
| *Centella asiatica* (water soluble extract) | 0.50 |
| D-panthenol | 1.00 |
| Acrylates/Palmeth-25 acrylate copolymer | 3.00 |
| Sodium hydroxide | 0.015 |
| Water | qs |

Method of Manufacture

To water add polyquaternium-10, EDTA tetra sodium salt, citric acid and quaternium 80. Add sodium laureth sulphate and cocamidopropyl betaine. Mix together phenoxyethanol, methyl parabens and propyl parabens and heat to 50° C. until dissolved. Add to main bulk. Add d-panthenol, amodimthicone and extract and sodium ascorbyl phosphate. Add acrylates/palmeth-25 acrylate copolymer (pre dispersed in a little water) and cocoamphoacetate. Add sodium hydroxide.

Example 16

Shampoo Formulation

| Ingredient | % w/w |
| --- | --- |
| Sodium laureth sulphate | 4.00 |
| Cocamidopropyl betaine | 1.20 |
| Sodium cocoamphoacetate | 2.40 |
| Citric acid | 0.15 |
| EDTA tetra sodium salt | 0.02 |
| Polyquaternium-10 | 0.30 |
| Propyl parabens | 0.10 |
| Methyl parabens | 0.20 |
| Phenoxyethanol | 0.85 |
| Quaternium 80 | 0.40 |
| Amodimethicone | 2.00 |
| Green coffee extract (4% dry weight aq extract) | 5.00 |
| *Centella asiatica* (water soluble extract) | 0.50 |
| *Rosmarinus officinalis* extract | 0.30 |
| Sodium ascorbyl phosphate | 0.30 |
| D-panthenol | 1.00 |
| Acrylates/Palmeth-25 acrylate copolymer | 3.00 |
| Sodium hydroxide | 0.015 |
| Water | qs |

Method of Manufacture

To water add polyquaternium-10, EDTA tetra sodium salt, citric acid and quaternium 80. Add sodium laureth sulphate and and cocamidopropyl betaine. Mix together phenoxyethanol, methyl parabens and propyl parabens and heat to 50° C. until dissolved. Add to main bulk. Add d-panthenol, amodimthicone, extracts and sodium ascorbyl phosphate. Add acrylates/palmeth-25 acrylate copolymer (pre dispersed in a little water) and Cocoamphoacetate. Add sodium hydroxide.

Example 17

Conditioner Formulation

| Ingredient | % w/w |
| --- | --- |
| Cetyl Alcohol | 6.00 |
| Cetrimonium chloride | 3.00 |
| Glyceryl monostearate | 0.50 |
| Glycerin | 0.50 |
| Silicone fluid (1000 cs) | 0.50 |
| Sodium citrate | 0.04 |
| Propylene glycol | 0.50 |
| Phenoxyethanol | 0.60 |
| Green coffee extract (4% dry weight aq extract) | 5.00 |
| *Centella asiatica* (oil soluble extract) | 0.50 |
| Water | qs |

Method of Manufacture

Mix together water, cetrimonium chloride, sodium citrate and propylene glycol with stirring. Heat to 70-75° C. In a separate vessel put glyceryl monsteaarate, cetyl alcohol, phenoxethanol, glycerin and silicone fluid. Heat to 70-75° C. Add oil phase to water and homogenising for about 1 minute. Stir cool to below 40° C. Add green coffee extract (4% dry weight aq extract) and *Centella asiatica* extract.

Example 18

Conditioner Formulation

| Ingredient | % w/w |
| --- | --- |
| Cetyl alcohol | 6.00 |
| Cetrimonium chloride | 3.00 |
| Glyceryl monostearate | 0.50 |
| Glycerin | 0.50 |
| Silicone fluid (1000 cs) | 0.50 |
| Sodium citrate | 0.04 |
| Propylene glycol | 0.50 |
| Phenoxyethanol | 0.60 |
| Green coffee extract (4% dry weight aq extract) | 5.00 |
| *Rosmarinus officinalis* extract | 0.30 |
| Water | qs |

Method of Manufacture

Mix together water, cetrimonium chloride, sodium citrate and propylene glycol with stirring. Heat to 70-75° C. In a separate vessel put glyceryl monosteaarate, cetyl alcohol, phenoxethanol, glycerin and silicone fluid. Heat to 70-75° C. Add oil phase to water and homogenising for about 1 minute. Stir cool to below 40° C. Add green coffee extract (4% dry weight aq extract) and *Rosmarinus officinalis* extract.

Example 19

Conditioner Formulation

| Ingredient | % w/w |
| --- | --- |
| Cetyl alcohol | 6.00 |
| Cetrimonium chloride | 3.00 |
| Glyceryl monostearate | 0.50 |
| Glycerin | 0.50 |
| Silicone fluid (1000 cs) | 0.50 |
| Sodium citrate | 0.04 |
| Propylene glycol | 0.50 |
| Phenoxyethanol | 0.60 |
| Sodium ascorbyl phosphate | 0.30 |
| *Centella asiatica* (oil soluble extract) | 0.50 |
| Water | qs |

Method of Manufacture

Mix together water, cetrimonium chloride, sodium citrate and propylene glycol with stirring. Heat to 70-75° C. In a separate vessel put glyceryl monosteaarate, cetyl alcohol, phenoxethanol, glycerin and silicone fluid. Heat to 70-75° C. Add oil phase to water and homogenising for about 1 minute. Stir cool to below 40° C. Add sodium ascorbyl phosphate and *Centella asiatica* extract.

Example 20

Conditioner Formulation

| Ingredient | % w/w |
| --- | --- |
| Cetyl alcohol | 6.00 |
| Cetrimonium chloride | 3.00 |
| Glyceryl monostearate | 0.50 |
| Glycerin | 0.50 |
| Silicone fluid (1000 cs) | 0.50 |
| Sodium citrate | 0.04 |
| Propylene glycol | 0.50 |
| Phenoxyethanol | 0.60 |
| Green coffee extract (4% dry weight aq extract) | 5.00 |
| *Centella asiatica* (oilsoluble extract) | 0.50 |
| *Rosmarinus officinalis* extract | 0.30 |
| Sodium ascorbyl phosphate | 0.30 |
| Water | qs |

Method of Manufacture

Mix together water, cetrimonium chloride, sodium citrate and propylene glycol with stirring. Heat to 70-75° C. In a separate vessel put glyceryl monosteaarate, cetyl alcohol, phenoxethanol, glycerin and silicone fluid. Heat to 70-75° C. Add oil phase to water and homogenising for about 1 minute. Stir cool to below 40° C. Add green coffee extract (4% dry weight aq extract), *Centella asiatica* extract, Rosmarinus officinalis extract and sodium ascorbyl phosphate.

Measurement of inhibition of interleukin-2 (IL-2) production by green coffee and *Centella asiatica* extracts The potential for the extracts to reduce/prevent hair loss or promote hair growth were assessed by an IL-2 inhibition assay. IL-2 has been associated with inhibition of hair growth and promotion of hair loss.

IL-2 Inhibition Methodology

Human lymphocytes were extracted from blood and cultured using standard techniques. A preliminary trial was carried out to ensure that test cells were able to produce IL-2 when stimulated with phytohaemogluttinin (pha), a known IL-2 promoter, and also for this stimulation to be inhibited using Cyclosporin A (CsA) which is a known inhibitor of IL-2 production. Results are shown in Table 1.

TABLE 1

| | IL-2 (pg/ml) |
| --- | --- |
| Cells alone | 32 |
| Cells + pha | >1000 |
| Cells + pha + CsA | 10 |

Following this confirmation of the capability of the cells to produce IL-2, studies using the extracts were carried out using the same methodology, but with the extracts replacing CsA. Results are shown in Table 2 and expressed as % IL-2 inhibition compared to control.

Control=50% denatured ethanol, 50% propylene glycol.

All materials were used at 1 in 1000 dilution.

TABLE 2

| | % |
| --- | --- |
| Control | 0 |
| Green Coffee | −6 |
| *Centella asiatica* | 10 |
| Green Coffee and *Centella asiatica* | 32 |

The results show that the IL-2 inhibitory effect of the combination of green coffee extract and *Centella asiatica* extract is greater than the sum of the inhibitory effects of the two extracts separately. Addition of *Rosmarinus officinalis* extract and sodium ascorbyl phosphate showed inhibition of IL-2 compared to the control of 88%.

Preliminary Analysis of Data after 3 Months

A cohort of male and female volunteers were randomly assigned either placebo or test hair growth product, wherein the formulation of the test hair growth product is given in Example 4, and the placebo is the same formulation minus the actives: green coffee, *Centella asiatica* , sodium ascorbyl phosphate and rosemary extract. At baseline the hair condition, thinning and growth rate were assessed by a trichologist, self perception and image analysis. 67 subjects were still present for the 3 months assessment of hair growth effects of the placebo and test products. The tables below summarise the results following a preliminary analysis.

TABLE 3

| Mean score | age | Years thinning | Hair condition change | Condition Improved (% yes/no) | Hair shedding change |
| --- | --- | --- | --- | --- | --- |
| Placebo | 49.2 | 10 | 0.208 | 25/75 | 0.271 |
| Test | 49.5 | 7.7 | 0.412 | 41.2/58.8 | 0.588 |
| T-test* | 0.929 | 0.438 | 0.331 | 0.239 | 0.245 |

TABLE 4

| Mean score | Hair shedding Improved (% yes/no) | Trichologist hair growth change (% yes/no) | Volunteers hair growth change (% yes/no) | Overall improvement | Image analysis of hair growth rate(% growth) |
|---|---|---|---|---|---|
| Placebo | 37.5/62.5 | 33/67 | 41.7/58.3 | 1.375 | 28.1 |
| Test | 52.9/47.1 | 41.2/58.8 | 52.3/47.1 | 1.882 | 37.7 |
| T-test* | 0.242 | 0.239 | 0.242 | 0.202 | 0.23 |

TABLE 5

| Mean Hamilton score** - men only (negative change = growth) | 0 mths | 3 mths | Change |
|---|---|---|---|
| Placebo | 3.4 | 3.7 | 0.44 |
| test | 4 | 3.7 | −0.094 |
| T-test* | | | 0.085 |

*T-test refers to the Student's t-test, a statistical method used to compare two groups of data to determine whether changes observed are due to chance. A T-test value of less than 0.05 (or 5%) is taken to mean that the data is statistically significant and therefore unlikely to be due to chance.
**The Hamilton scale is a widely accepted clinical scale used to assess the degree of male pattern baldness. A Hamilton score of 1 indicates change to frontal hairline and slight changes at temples. A Hamilton score of 3 indicates the start of a bald spot on the scalp and a score of 7 indicates a shiny dome.

The invention claimed is:

1. A composition for the treatment of hair loss and/or the promotion of hair growth comprising:
   a) *Centella asiatica* extract at a concentration in the range of 0.05% to 5% by weight,
   b) green coffee extract at a concentration in the range of 0.02% to 0.6% by weight, and
   c) at least one of *Rosmarinus officinalis* extract and sodium ascorbyl phosphate at a concentration in the range of 0.005% to 10% by weight; wherein said composition further comprising a dermatologically acceptable carrier.

2. The composition as claimed in claim 1, wherein the composition is substantially free of caffeine.

3. The composition as claimed in claim 1, wherein the composition is substantially free of creatine compound.

4. The composition as claimed in claim 1, wherein the concentration of *Centella asiatica* extract is at least 0.1% by weight.

5. The composition as claimed in claim 1, wherein the concentration of *Centella asiatica* extract is less than 5% by weight.

6. The composition as claimed in claim 1, wherein the concentration of *Centella asiatica* extract is less than 0.1% by weight.

7. The composition as claimed in claim 1, wherein the concentration of *Centella asiatica* extract is in the range of 0.1% to 2% by weight.

8. The composition as claimed in claim 1, wherein the concentration of green coffee extract is at least 0.04% by weight.

9. The composition as claimed in claim 1, wherein the concentration of green coffee extract is less than 0.6% by weight (dwt).

10. The composition as claimed in claim 1, wherein the concentration of green coffee extract is less than 0.3% by weight (dwt).

11. The composition as claimed in claim 1, wherein the concentration of green coffee extract is in the range of 0.04 to 0.3% by weight (dwt).

12. The composition as claimed in claim 1, wherein said at least one of *Rosmarinus officinalis* extract and sodium ascorbyl phosphate are present in said composition in a concentration in the range of 0.1% to 2% by weight.

13. The composition as claimed in claim 1, further comprising one or more excipients selected from the group consisting of surfactants, excipients to enhance texture and skin-feel, vitamins, natural extracts, preservatives, chelating agents, perfumes and coloring.

14. The composition according to claim 1, wherein the composition is in the form of a gel, lotion shampoo or conditioner.

15. A method for the treatment of hair loss, the promotion of hair regrowth, and/or improvement in hair quality comprising applying the composition of claim 1 to the scalp of a subject in need thereof.

* * * * *